(12) United States Patent
de Boer et al.

(10) Patent No.: US 10,416,389 B2
(45) Date of Patent: Sep. 17, 2019

(54) SYSTEM AND METHOD ASSOCIATED WITH A PHOTONIC INTEGRATED CIRCUIT

(71) Applicant: Nederlandse Organisatie voor toegepast-natuurwetenschappelijk onderzoek TNO, 's-Gravenhage (NL)

(72) Inventors: Bart Michiel de Boer, 's-Gravenhage (NL); Peter Johan Harmsma, 's-Gravenhage (NL)

(73) Assignee: Nederlandse Organisatie Voor Toegepast-Natuurwetenschappelijk Onderzoek Tno, 'S-Gravenhage (NL)

( * ) Notice: Subject to any disclaimer, the term of this patent is extended or adjusted under 35 U.S.C. 154(b) by 0 days.

(21) Appl. No.: 15/315,022

(22) PCT Filed: Jun. 3, 2015

(86) PCT No.: PCT/NL2015/050397
§ 371 (c)(1),
(2) Date: Nov. 30, 2016

(87) PCT Pub. No.: WO2015/187014
PCT Pub. Date: Dec. 10, 2015

(65) Prior Publication Data
US 2017/0205581 A1 Jul. 20, 2017

(30) Foreign Application Priority Data
Jun. 4, 2014 (EP) .................... 14171129

(51) Int. Cl.
*G02B 6/293* (2006.01)
*G02B 6/30* (2006.01)
(Continued)

(52) U.S. Cl.
CPC ..... *G02B 6/29338* (2013.01); *G01M 11/3181* (2013.01); *G02B 6/124* (2013.01);
(Continued)

(58) Field of Classification Search
CPC .... G01C 19/72; G01C 19/721; G01C 19/722; G02B 6/1225; G02B 6/124; G02B 6/125;
(Continued)

(56) References Cited

U.S. PATENT DOCUMENTS 7,378,861 B1 5/2008 Malendevich et al.
2003/0235370 A1 12/2003 Taillaert et al.
(Continued)

OTHER PUBLICATIONS

Bogaerts, Wim et al. "A polarization-diversity wavelength duplexer circuit in silicon-on-insulator photonic wires". Optics Express, vol. 15, No. 4, Feb. 19, 2007, pp. 1567-1578.*
(Continued)

*Primary Examiner* — Michael A Lyons
(74) *Attorney, Agent, or Firm* — Hoffmann & Baron, LLP (57) ABSTRACT

The present disclosure concerns a photonic integrated circuit (10) and a method for interrogating a ring resonator (3) comprised therein. The circuit (10) comprises an optical port (4) for coupling light (L) into and out of the circuit (10). The circuit (10) further comprises a first waveguide (1) for receiving light (L1) from the optical port (4), and a second waveguide (2) for sending back light to the optical port (4). The ring resonator (3) is arranged between the first waveguide (1) and the second waveguide (2) for coupling a resonant wavelength ($\lambda$) of the light therein between. The optical port (4) comprises a polarization splitting coupler for coupling light of a first polarization (P1) to and from the first waveguide (1) and coupling light of a second polarization (P2), orthogonal to the first polarization (P1), to and from the second waveguide (2).

13 Claims, 3 Drawing Sheets (51) Int. Cl.
*G02B 6/12* (2006.01)
*G02B 6/122* (2006.01)
*G01M 11/00* (2006.01)
*G02B 6/124* (2006.01)
*G02B 6/125* (2006.01)
*G02B 6/126* (2006.01)
*G02B 6/27* (2006.01)
*G01N 21/45* (2006.01)

(52) U.S. Cl.
CPC ............. *G02B 6/125* (2013.01); *G02B 6/126* (2013.01); *G02B 6/12007* (2013.01); *G02B 6/1225* (2013.01); *G02B 6/2726* (2013.01); *G02B 6/2773* (2013.01); *G02B 6/29343* (2013.01); *G02B 6/30* (2013.01); *G02B 6/305* (2013.01); *G01N 21/45* (2013.01); *G01N 2021/458* (2013.01); *G02B 2006/1213* (2013.01); *G02B 2006/1215* (2013.01); *G02B 2006/12107* (2013.01); *G02B 2006/12109* (2013.01); *G02B 2006/12138* (2013.01); *G02B 2006/12147* (2013.01)

(58) Field of Classification Search
CPC .... G02B 6/126; G02B 6/2726; G02B 6/2733; G02B 6/2773; G02B 6/29338; G02B 6/29343; G02B 6/30; G01B 2290/70
See application file for complete search history.

(56) References Cited

U.S. PATENT DOCUMENTS

| | | | |
|---|---|---|---|
| 2004/0184156 A1* | 9/2004 | Gunn, III | G02B 6/1228 359/629 |
| 2005/0035278 A1 | 2/2005 | Margalit et al. | |
| 2010/0265504 A1* | 10/2010 | Kopp | G02B 6/12002 356/364 |
| 2010/0322555 A1 | 12/2010 | Vermeulen et al. | |
| 2011/0116735 A1* | 5/2011 | Baets | G01D 5/268 385/12 |
| 2012/0002971 A1* | 1/2012 | Doerr | G02B 6/124 398/115 |
| 2015/0345950 A1* | 12/2015 | Yao | G01C 19/72 356/365 |

OTHER PUBLICATIONS

Bogaerts et al., "Silicon-on-insulator nanophotonics," Invited Paper, Integrated Optics: Theory and Applications, ed. by Pustelny et al., Proc. of SPIE, vol. 5956 (2005), 59560R-1-59560R-15.

Fujiwara et al., "Optical waveguide resonator for one-port refractive index sensing," Copyright 2013 The Japan Society of Applied Physics, 18th Microoptics Conference (MOC'13), Tokyo, Japan, Oct. 27-30, 2013.

* cited by examiner

SYSTEM AND METHOD ASSOCIATED WITH A PHOTONIC INTEGRATED CIRCUIT

This application is the U.S. National Phase of, and Applicants claim priority from, International Patent Application Number PCT/NL2015/050397 filed 3 Jun. 2015, which claims priority from EP 14171129.1 filed 4 Jun. 2014, each of which is incorporated herein by reference.

TECHNICAL FIELD AND BACKGROUND

The present disclosure relates to a photonic integrated circuit comprising a ring resonator and a method for interrogating a ring resonator in a photonic integrated circuit.

A photonic integrated circuit (IC) also known as an integrated optical circuit is a device that integrates photonic functions. Light traversing the circuit can be guided and/or processed by the circuit. One example of a photonic integrated circuit comprises a ring resonator arranged in proximity between a first waveguide and a second waveguide. Light in the waveguides may be coupled to the ring, e.g. by an evanescent field. In this way light may travel via the ring from the first waveguide to the second waveguide. The ring may have one or more resonant wavelengths that are selectively or predominantly passed between the waveguides. A resonant wavelength of the ring can depend on a physical parameter influencing the ring. Accordingly, the ring can exhibit a spectral signature that can be used to quantify said physical parameter, e.g. temperature, pressure, chemical data, etc.

The circuit can be interrogated (read out) by an analyser. For example, the analyser can couple light into the first waveguide of the circuit and detect output light from the second waveguide of the circuit to measure the spectral signature of the optical sensing element and quantify the physical parameter. The analyser can be a separate instrument for interrogating the photonic circuit, e.g. integrated on a chip. In this way different circuits can be interrogated by a single instrument. To provide a flexible connection between the analyser and circuit, light can be free-space coupled into the circuit via an optical port, e.g. a vertical grating coupler. For example, the analyser comprises an objective lens, or an optical fibre that is brought in close proximity to the optical port.

Typically, separate ports are used to couple light in and out of the circuit. In order to reduce complexity, it can be advantageous to have as few optical connections as possible. This can make alignment procedures between the circuit and analyser easier. For instance if a single port can be employed to couple light in and out of the circuit, the coupling can be more tolerant to rotation of the circuit e.g. with respect to the fibre around the optical axis. This can make implementation in a hand-held device, e.g. for point-of-care diagnostics more feasible. It has been tried to interrogate a ring resonator via a single conventional vertical grating coupler. However, the response was found to be of poor quality.

Accordingly, there is a desire to improve response quality of the photonic integrated circuit comprising a ring resonator interrogated via a single optical port.

SUMMARY

A first aspect of the present disclosure provides a photonic integrated circuit comprising an optical port for coupling light into and out of the circuit; a first waveguide arranged for receiving light from the optical port coupled into the circuit; a second waveguide arranged for sending back light to the optical port to be coupled out of the circuit; a ring resonator arranged between the first waveguide and the second waveguide for coupling a resonant wavelength of the light from the first waveguide to the second waveguide; wherein the optical port comprises a polarization splitting coupler arranged for coupling light of a first polarization to and from the first waveguide and coupling light of a second polarization, orthogonal to the first polarization, to and from the second waveguide.

The inventors find that the response quality of the photonic integrated circuit can deteriorate as a result of reflections between the analyser and circuit. When using an optical fibre to interrogate the circuit, the fibre facet can reflect a small part of the light (e.g. four percent) received from the circuit back into the circuit. For ring resonance wavelengths, the ring can act as a mirror. Light coupled into the optical port is coupled back via the ring into the port and into the fibre. Hence, the fibre facet and ring can form a cavity causing interference of the response.

By using a polarization splitting coupler as the optical port, the interference can be reduced. The polarization of measurement light exiting the optical port is rotated with respect to the light entering the optical port. When part of the measurement light exiting the optical port is reflected back into the circuit by the analyser facet (optical interface), this reflection light is sent to the second waveguide due to its rotated polarization. The reflection light thus travels in the opposite direction through the circuit to have its polarization rotated back again. The reflection light then exits the port again but now with a different polarization than the measurement light. Due to its different polarization the reflection light no longer interferes with the measurement light. Accordingly, response quality of the photonic integrated circuit can be improved.

By having the circuit form a looped path beginning and ending at the optical port, light of the first polarization coupled into the optical port and traversing the looped path can be coupled out of the optical port as light of the second polarization and vice versa. By having the first waveguide and the second waveguide form an intersection at a right angle, the polarization of light exiting the second waveguide can be rotated with respect to light entering the first waveguide. By providing a two-dimensional diffraction grating structure, light having the first polarization can be coupled to the first waveguide and light having the second polarization can be coupled to the second waveguide. By providing a photonic crystal, light having the first polarization can be coupled to the first waveguide and light having the second polarization coupled to the second waveguide.

By providing a plurality of ring resonators in the circuit, each of the ring resonators can couples a respective resonant wavelength of the light from the first waveguide to the second waveguide. In this way a plurality of parameters can be measured. For example, a plurality of ring resonators can be arranged in between a length of the first waveguide and length of the second waveguide. Alternatively or in addition, in one embodiment, one or both of the first waveguide and/or second waveguide comprises a splitter for splitting the respective waveguide into a plurality of optical paths. In this way the first and/or second waveguides can be coupled to a plurality of ring resonators.

The photonic integrated circuit as described herein can be advantageously incorporated in an optical system. The optical system may comprise an analyser for interrogating the circuit. By providing the analyser with an optical fibre, light can be easily transmitted to the optical port. Advantageously, the same fibre can be used both for transmitting the source light with the first polarization to the optical port and for receiving measurement light from the optical port with the second polarization. By providing a polarizing beam splitter in the analyser, measurement light received from the optical port can be separated from interfering reflection light. For example, a sensor can be arranged to measure only light received from the optical port having the second polarization. By transmitting light to the optical port at a low angle with respect to a normal of the optical port, e.g. the two dimensional structure thereof, the polarization can be better maintained without skewing while sending and receiving the light between the analyser and the port. Preferably the angle is lower than 15 degrees, more preferably lower than 10 degrees, e.g. between 7-10 degrees.

A second aspect of the present disclosure provides a method for interrogating a ring resonator in a photonic integrated circuit, the method comprising coupling light having a first polarization into an optical port of the circuit; receiving the light from the optical port into a first waveguide of the circuit; coupling a resonant wavelength of the light from the first waveguide to a second waveguide via the ring resonator; sending back the light with the resonant wavelength via the second waveguide to the optical port; and coupling out the light with the resonant wavelength from the optical port; wherein the optical port comprises a polarization splitting coupler that couples light having the first polarization to and from the first waveguide and couples light having a second polarization, orthogonal to the first polarization, to and from the second waveguide.

By splitting the light received from the optical port according to its polarization and measuring the split light having the second polarization, interference from the reflection light, having the first polarization, can be reduced. Accordingly, response quality of the photonic integrated circuit can be improved. By providing an optical fibre for transmitting and receiving light to and from the optical port, the connection can be more flexible.

It is noted that prior art document US 2003/0235370 describes optical couplers for providing a structure to make polarization independent photonic integrated circuits. This is an entirely different purpose than to improve response quality of the photonic integrated circuit comprising a ring resonator interrogated via a single optical port. However, the inventors recognize that the optical couplers described in said prior art document can also be used as a polarization splitting coupler in a photonic integrated circuit according to the present disclosure to improve response quality.

BRIEF DESCRIPTION OF DRAWINGS

These and other features, aspects, and advantages of the apparatus, systems and methods of the present disclosure will become better understood from the following description, appended claims, and accompanying drawing wherein:

DESCRIPTION OF EMBODIMENTS

Unless otherwise defined, all terms (including technical and scientific terms) used herein have the same meaning as commonly understood by one of ordinary skill in the art to which this invention belongs as read in the context of the description and drawings. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some instances, detailed descriptions of well-known devices and methods may be omitted so as not to obscure the description of the present systems and methods. Terminology used for describing particular embodiments is not intended to be limiting of the invention. As used herein, the singular forms "a", "an" and "the" are intended to include the plural forms as well, unless the context clearly indicates otherwise. The term "and/or" includes any and all combinations of one or more of the associated listed items. It will be understood that the terms "comprises" and/or "comprising" specify the presence of stated features but do not preclude the presence or addition of one or more other features. It will be further understood that when a particular step of a method is referred to as subsequent to another step, it can directly follow said other step or one or more intermediate steps may be carried out before carrying out the particular step, unless specified otherwise. Likewise it will be understood that when a connection between structures or components is described, this connection may be established directly or through intermediate structures or components unless specified otherwise. All publications, patent applications, patents, and other references mentioned herein are incorporated by reference in their entirety. In case of conflict, the present specification, including definitions, will control.

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. The description of the exemplary embodiments is intended to be read in connection with the accompanying drawings, which are to be considered part of the entire written description. In the drawings, the absolute and relative sizes of systems, components, layers, and regions may be exaggerated for clarity. Embodiments may be described with reference to schematic and/or cross-section illustrations of possibly idealized embodiments and intermediate structures of the invention. In the description and drawings, like numbers refer to like elements throughout. Relative terms as well as derivatives thereof should be construed to refer to the orientation as then described or as shown in the drawing under discussion. These relative terms are for convenience of description and do not require that the system be constructed or operated in a particular orientation unless stated otherwise.

Figure 1:
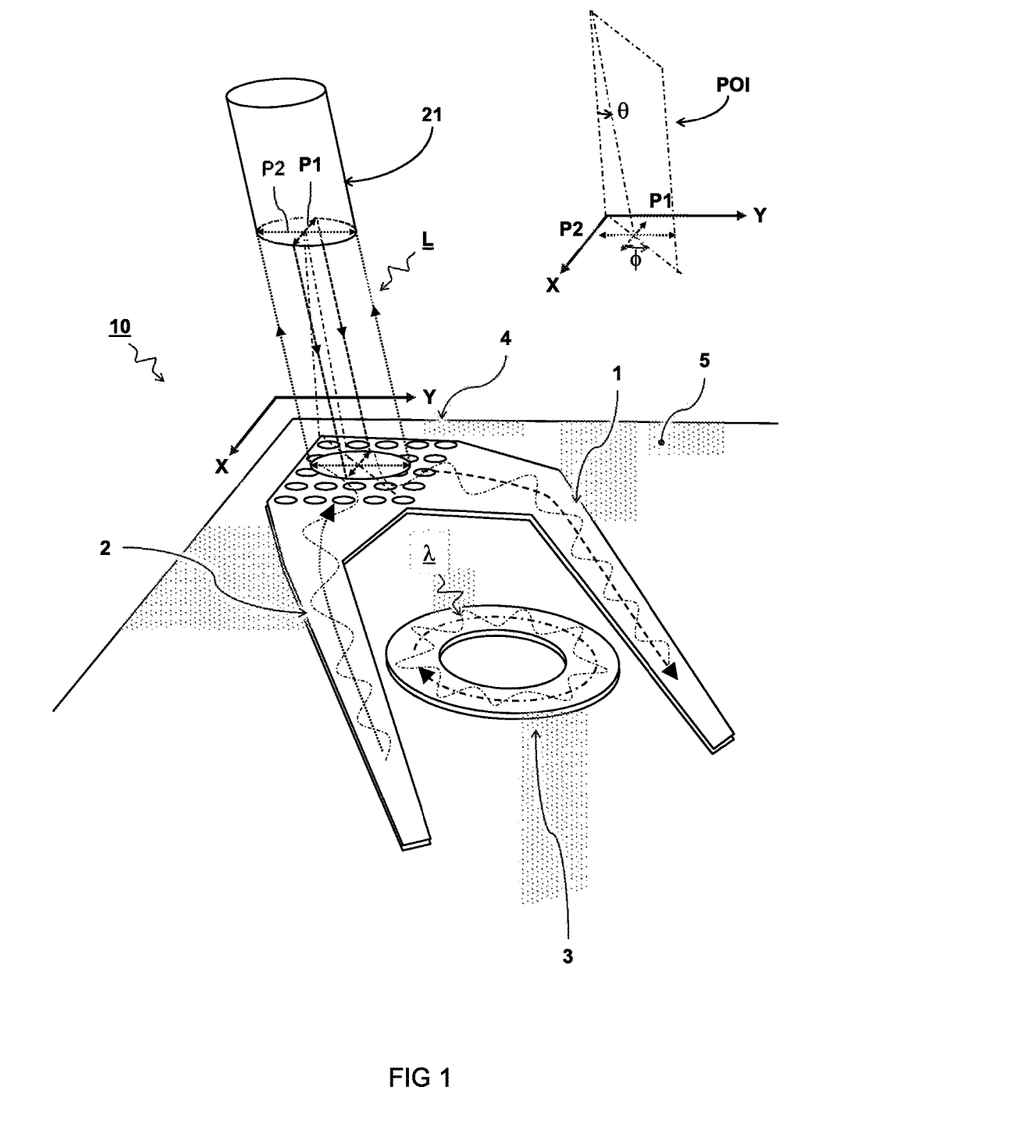
FIG. 1 shows a schematic perspective view of an embodiment of a photonic integrated circuit comprising a ring resonator interrogated via a single optical port.

FIG. 1 shows a photonic integrated circuit 10. The circuit 10 comprises an optical port 4 for coupling light L into and out of the circuit 10. The circuit 10 further comprises a first waveguide 1 arranged for receiving light L1 from the optical port 4 coupled into the circuit 10. The circuit 10 further comprises a second waveguide 2 arranged for sending back light to the optical port 4. The light can thus be coupled back out of the circuit 10 via the same optical port 4. The circuit 10 further comprises a ring resonator 3 arranged between the first waveguide 1 and the second waveguide 2. The ring resonator 3 can couple a resonant wavelength λ of the light from the first waveguide 1 to the second waveguide 2. The optical port 4 comprises a polarization splitting coupler. The polarization splitting coupler 4 is arranged for coupling light of a first polarization P1 to and from the first waveguide 1 and coupling light of a second polarization P2 to and from the second waveguide 2. The second polarization P2 is orthogonal to the first polarization P1 having a relative angle close to 90 degrees, e.g. between 85-95 degrees. The more orthogonal the polarizations P1 and P2, the better they can be separated.

In one embodiment, the photonic integrated circuit 10 is formed on a substrate 5, e.g. as part of an optical chip. The chip can be interrogated by source light L, e.g. emitted from an optical fibre 21. In the embodiment shown, the source light L impinging the optical port 4 has a first polarization P1 with its electric field primarily or exclusively in the "X" direction as indicated. After the source light L is coupled into the circuit by the optical port 4, it is directed to the first waveguide 1. The electric field oscillates in the plane of the substrate 5, which is commonly referred to as 'TE polarized'. Light in the first waveguide 1 may couple to the ring resonator 3. From the ring resonator 3, light may couple to the second waveguide 2. The effective coupling from waveguide 1 to waveguide 2 via the ring is typically most efficient for resonant wavelengths λ of the ring, e.g. wherein an integer number of wavelengths of the light fits a circumference of the ring. Light is sent back to the optical port 4 via the second waveguide 2. It is noted that, while traversing the circuit, the polarization of the light has not changed, and is still TE in this embodiment: the electric field still oscillates in the plane of the substrate 5. The TE-polarized light coming from waveguide 2 will be coupled into the fiber by optical port 4 such that in the fiber the light has a polarization P2, with its electric field primarily or exclusively in the "Y" direction as indicated, i.e. the second polarization P2 of the measurement light is transverse to the first polarization P1 of the source light.

In one embodiment, the first waveguide 1, ring resonator 3, and second waveguide 2 form a looped path beginning and ending at the optical port 4. Light of the first polarization P1 coupled into the optical port 4 and traversing the looped path is coupled out of the optical port 4 as light of the second polarization P2. In one embodiment, the first waveguide 1 and the second waveguide 2 form an intersection at the optical port 4 wherein a direction of a light path of the first waveguide 1 from the optical port 4 is transverse to a direction of a light path of the second waveguide 2 to the optical port 4. In other words, the first and second waveguides 1,2 form a right angle intersection.

The polarization splitting coupler 4, is arranged to couple out the second polarization P2 in the approximately the same direction as where the source light came from. Accordingly, the same optical fibre 21 can be used for capturing the measurement light. Preferably, the optical fibre 21 is arranged for transmitting light to the optical port 4 at a relatively low angle θ with respect to a normal of the optical port 4. In one embodiment, the optical port 4 comprises a two-dimensional diffraction grating structure wherein an optical fibre 21 or other light source is arranged for transmitting light to the optical port 4 at an angle θ of less than 15 degrees with respect to a normal of the two-dimensional diffraction grating structure. In one embodiment, the plane of incidence (POI) of the source light L is diagonal with respect to the first polarization P1 and second polarization P2, preferably at an angle Φ of 45 degrees with respect to both the first polarization P1 and second polarization P2.

In one embodiment, the optical port 4 comprises a two dimensional array of periodically arranged structures, wherein the array is arranged to couple the light of the first polarization P1 along a first dimension of the array and arranged to couple to the light of the second polarization P2 along a second dimension of the array transverse to the first dimension.

In one embodiment, the optical port 4 comprises a diffraction grating structure for coupling light having the first polarization P1 to the first waveguide 1 and coupling light having the second polarization P2 to the second waveguide 2. The diffraction grating structure can be a periodic, an essentially or substantially periodic structure, or a non-periodic structure. In one embodiment, the diffraction grating structure comprises a periodic grating structure with less than 200 periods, preferably less than 100 periods, more preferably less than 70 periods, more preferably less than 20 periods. In one embodiment, the diffraction grating structure is a two-dimensional grating. In one embodiment, the two-dimensional grating comprises a periodic refractive index modulation. In one embodiment, the periodic refractive index modulation comprises an array of holes and/or rods.

In one embodiment, the optical port 4 comprises a photonic crystal. In one embodiment, the photonic crystal is a two-dimensional photonic crystal. In one embodiment, the two-dimensional photonic crystal comprises a square lattice structure. A photonic crystal may refer to a periodic structure of which the refractive index is periodic, typically with high contrast. To influence diffraction of light, the periodicity is of an order similar to the wavelength of that light. The photonic crystal may couple light having the first polarization P1 to the first waveguide 1 and couple light having the second polarization P2 to the second waveguide 2.

In one embodiment, the first and/or second waveguides 1,2 comprise ridge waveguides. In one embodiment, the waveguides comprise a tapered portion. The tapered portion can function as a lateral spot size converter. In one embodiment, the first and/or second waveguides 1,2 comprise slab waveguides horizontally formed on the substrate 5. In one embodiment, the slab waveguides comprises a top layer with a lower refractive index than one or more underlying layers.

Figure 2:
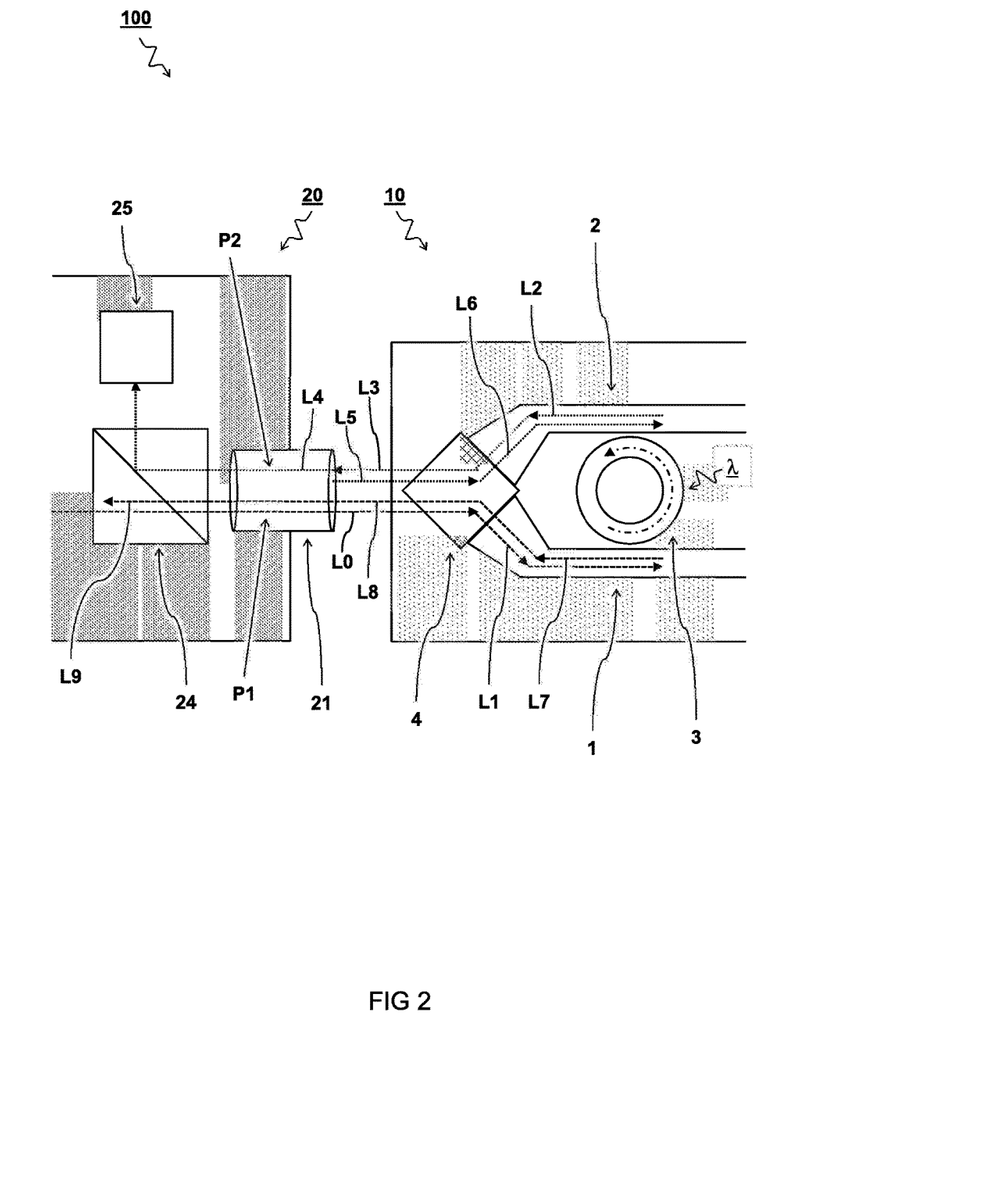
FIG. 2 shows a schematic view of an embodiment an optical system comprising an analyser and a photonic integrated circuit.

FIG. 2 shows an optical system 100. The system 100 comprises a photonic integrated circuit 10 as described herein and an analyser 20 for interrogating the circuit 10.

In one embodiment, the analyser 20 comprises an optical fibre 21 for transmitting light L0 to the optical port 4 with the first polarization P1 and for receiving light L3,L8 from the optical port 4 with the second polarization P2. In the embodiment shown, source light L0 with first polarization P1 enters the circuit 10 via optical port 4. The optical port 4 comprises a polarization splitting coupler that sends the light with first polarization P1 into the first waveguide 1. Light L1 in the first waveguide 1 having a resonant wavelength λ is coupled to the second waveguide 2 via ring resonator 3. Light L2 in the second waveguide 2 is sent back to the optical port 4 to be coupled out from the circuit 10 with second polarization P2, transverse to the first polarization P1. The light L3 coupled out from the circuit 10 is sent back to the optical fibre 21. Most of the light L4 enters the optical fibre 21, while a small part L5 is reflected by an entry surface of the optical fibre 21. The reflection light L5, still having the second polarization P2, re-enters the circuit via optical port 4. The light L5 with the second polarization P2 is sent by the optical port 4 into the second waveguide 2. The reflection light L6 thus entering the second waveguide 2 couples back to the first waveguide 1 via the ring resonator 3. The reflection light L7 in the first waveguide 1 couples out of the circuit 10 via optical port 4 now having again the first polarization P1. The reflection light L8 with the first polarization P1 may also enter the optical fibre 21 as light L9. A second reflection of the light L8 at the interface of the optical fibre 21 may be neglected.

In one embodiment, the analyser 20 comprises a polarizing beam splitter 24 for separating light L9 received from the optical port 4 having the first polarization P1 from light L4 received from the optical port 4 having the second polarization P2. In this way the otherwise interfering reflection light can be discarded. In one embodiment, the analyser 20 comprises a sensor 25 arranged for measuring light L4 received from the optical port 4 having the second polarization P2.

In one embodiment, the analyser 20 comprises or couples to a light source (not shown). The light source may comprise a broadband light source or a narrowband light source. For example, measuring the spectral signature of the ring resonator 3 may comprise probing the circuit 10 with a broadband optical signal or a varying or constant narrowband optical signal and recording the spectral response of circuit 10.

In one aspect, the present disclosure provides a method for interrogating a ring resonator 3 in a photonic integrated circuit 10. The method comprises coupling light L0 having a first polarization P1 into an optical port 4 of the circuit 10. The method further comprises receiving the light L1 from the optical port 4 into a first waveguide 1 of the circuit 10. The method further comprises coupling a resonant wavelength $\lambda$ of the light L1 from the first waveguide 1 to a second waveguide 2 via the ring resonator 3. The method further comprises sending back the light L2 with the resonant wavelength $\lambda$ via the second waveguide 2 to the optical port 4. The method further comprises coupling out the light L3 with the resonant wavelength $\lambda$ from the optical port 4. The optical port 4 comprises a polarization splitting coupler that couples light having the first polarization P1 to (L0→L1) and from (L7→L8) the first waveguide 1 and couples light having a second polarization P2, orthogonal to the first polarization P1, to (L5→L6) and from (L2→L3) the second waveguide 2. In one embodiment, the method comprises splitting the light L3,L8 received from the optical port 4 according to its polarization P2,P1 and measuring the split light L4 having the second polarization P2. In one embodiment, the method comprises providing an optical fibre 21 for transmitting and receiving light to and from the optical port 4.

Figure 3A:
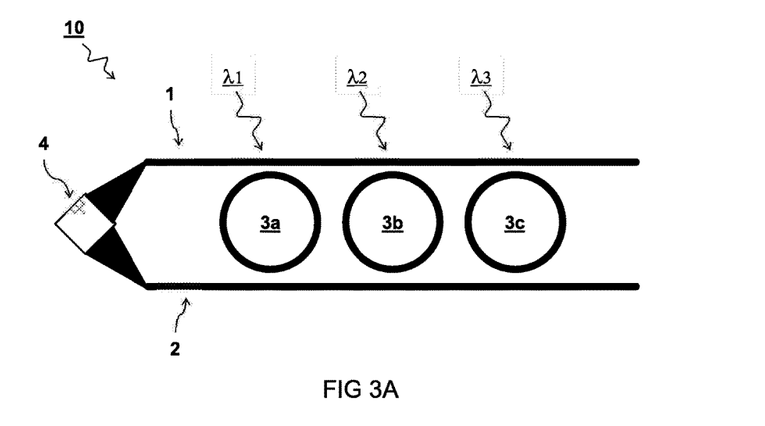
FIGS. 3A and 3B show schematic views of other embodiments of photonic integrated circuits.
Figure 3B:
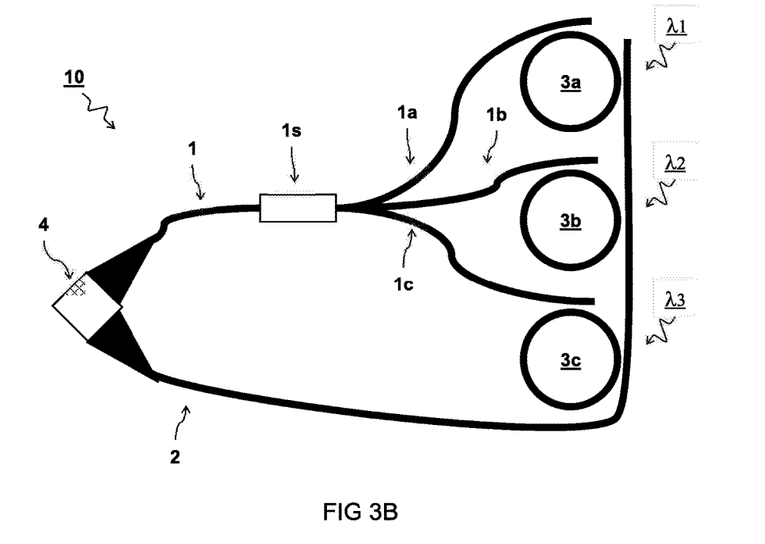

FIGS. 3A and 3B show other embodiments of a photonic integrated circuit 10. The circuits comprises a plurality of ring resonators 3a,3b,3c, wherein each of the ring resonators 3a,3b,3c couples a respective resonant wavelength $\lambda 1,\lambda 2,\lambda 3$ of the light from the first waveguide 1 to the second waveguide 2.

In the embodiment of FIG. 3A, the plurality of ring resonators 3a, 3b, 3c are arranged in between a length of the first waveguide 1 and length of the second waveguide 2.

In the embodiment of FIG. 3B, the first waveguide 1 comprises a splitter is for splitting the waveguide 1 into a plurality of optical paths 1a, 1b, 1c, for coupling to the plurality of ring resonators 3a,3b,3c. Alternatively or in addition also the second waveguide 2 may comprise a splitter (not shown)

For the purpose of clarity and a concise description, features are described herein as part of the same or separate embodiments. However, it will be appreciated that the scope of the invention may include embodiments having combinations of all or some of the features described. While embodiments were shown for a ring resonator between the first waveguide and second waveguide, alternatively, or in addition other optical structures can be arranged therein between, e.g. any (general) optical structure or combination of structures for coupling light from the first waveguide to the second waveguide, and/or vice versa can be envisaged. The optical structure (or combination of structures) which may replace the ring resonator or be added in combination with a ring resonator can e.g. be arranged to provide a specific optical functionality. For example, the optical structure may transmit and/or reflect a specific wavelength, which may be dependent on an external parameter such as temperature or stress. Alternatively, or in addition a second or further ring resonator or other optical structure can be arranged between the waveguides and/or between a first ring resonator and one or both of the waveguides. While embodiments were shown for an analyser comprising an optical fibre, also other means for delivering the light can be used, e.g. an objective lens. Also for other cases, interference by a reflection in the analyser may be alleviated.

Optical components may be combined or split up into one or more alternative components having similar function. The various elements of the embodiments as discussed and shown offer certain advantages, such as a providing a simple yet robust optical circuit. Of course, it is to be appreciated that any one of the above embodiments or processes may be combined with one or more other embodiments or processes to provide even further improvements in finding and matching designs and advantages. It is appreciated that this disclosure offers particular advantages for interrogating a ring resonator via a single optical port, and in general can be applied for other optical circuits wherein a single optical coupling is desired for interrogating a sensor, particularly in a looped circuit.

While the present systems and methods have been described in particular detail with reference to specific exemplary embodiments thereof, it should also be appreciated that numerous modifications and alternative embodiments may be devised by those having ordinary skill in the art without departing from the scope of the present disclosure. For example, embodiments wherein devices or systems are disclosed to be arranged and/or constructed for performing a specified method or function inherently disclose the method or function as such and/or in combination with other disclosed embodiments of methods or systems. Furthermore, embodiments of methods are considered to inherently disclose their implementation in respective hardware, where possible, in combination with other disclosed embodiments of methods or systems. Furthermore, methods that can be embodied as program instructions, e.g. on a non-transient computer-readable storage medium, are considered inherently disclosed as such embodiment.

Finally, the above-discussion is intended to be merely illustrative of the present systems and/or methods and should not be construed as limiting the appended claims to any particular embodiment or group of embodiments. The specification and drawings are accordingly to be regarded in an illustrative manner and are not intended to limit the scope of the appended claims. In interpreting the appended claims, it should be understood that the word "comprising" does not exclude the presence of other elements or acts than those listed in a given claim; the word "a" or "an" preceding an element does not exclude the presence of a plurality of such elements; any reference signs in the claims do not limit their scope; several "means" may be represented by the same or different item(s) or implemented structure or function; any of the disclosed devices or portions thereof may be combined together or separated into further portions unless specifically stated otherwise. The mere fact that certain measures are recited in mutually different claims does not indicate that a combination of these measures cannot be used to advantage. In particular, all working combinations of the claims are considered inherently disclosed.

The invention claimed is:

1. A photonic integrated circuit comprising:
an optical port for coupling source light into the circuit and coupling measurement light out of the circuit;
a first waveguide arranged for receiving the source light from the optical port coupled into the circuit;
a second waveguide arranged for returning the measurement light to the optical port for coupling out of the circuit; and
a ring resonator arranged between the first waveguide and the second waveguide for coupling a resonant wavelength of the source light from the first waveguide to the second waveguide to form the measurement light, wherein an integer number of resonant wavelengths of the light form a circumference of the ring;
wherein the optical port comprises a polarization splitting coupler arranged for:
coupling source light of a first polarization to the first waveguide; and
coupling measurement light of a second polarization, orthogonal to the first polarization from the second waveguide, wherein the first waveguide, the ring resonator, and the second waveguide form a looped path beginning and ending at the optical port, the first waveguide and the second waveguide intersecting at the optical port, a direction of the first waveguide being orthogonal to a direction of the second waveguide at the intersection, the source light of the first polarization coupled in the direction of the first waveguide, and returning at the intersection as the measurement light in the orthogonal direction after traversing the looped path, thereby rotating the polarization of the measurement light that exits the optical port after traversal of the looped path, as compared with polarization of the source light entering the optical port.

2. The photonic integrated circuit according to claim 1, wherein the optical port comprises a two-dimensional diffraction grating structure for coupling light having the first polarization to the first waveguide and coupling light having the second polarization to the second waveguide.

3. The photonic integrated circuit according to claim 1, wherein the optical port comprises a photonic crystal for coupling light having the first polarization to the first waveguide and coupling light having the second polarization to the second waveguide.

4. The photonic integrated circuit according to claim 1, wherein the circuit comprises a plurality of ring resonators, wherein each of the ring resonators couples a respective resonant wavelength of the light from the first waveguide to the second waveguide.

5. The photonic integrated circuit according to claim 1, wherein a plurality of ring resonators are arranged in between a length of the first waveguide and length of the second waveguide.

6. The photonic integrated circuit according to claim 1, wherein one or both of the first waveguide and/or second waveguide comprises a splitter for splitting the respective waveguide into a plurality of optical paths, for coupling to a plurality of ring resonators.

7. An optical system including a photonic integrated circuit, the optical system comprising:
an optical port for coupling source light into the circuit, and coupling measurement light out of the circuit, the circuit forming a looped path beginning and ending at the optical port;
a first waveguide arranged for receiving the source light from the optical port coupled into the circuit;
a second waveguide arranged for transmitting the measurement light back to the optical port for coupling out of the circuit;
a ring resonator arranged between the first waveguide and the second waveguide for coupling a resonant wavelength of the source light from the first waveguide to the second waveguide to form the measurement light, wherein an integer number of resonant wavelengths of the light form a circumference of the ring,
wherein the optical port comprises a polarization splitting coupler arranged for:
coupling source light of a first polarization to the first waveguide; and
coupling measurement light of a second polarization that is orthogonal to the first polarization from the second waveguide, wherein the first waveguide, the ring resonator, and the second waveguide form a looped path beginning and ending at the optical port, the first waveguide and the second waveguide intersecting at the optical port, a direction of the first waveguide being orthogonal to a direction of the second waveguide at the intersection, the source light of the first polarization coupled in the direction of the first waveguide, and returning at the intersection as the measurement light in the orthogonal direction after traversing the looped path, thereby rotating the polarization of the measurement light that exits the optical port after traversal of the looped path, as compared with polarization of the source light entering the optical port; and
an analyser operatively coupled to the photonic integrated circuit, for interrogating the circuit, wherein the analyser comprises an optical fibre for transmitting light to the optical port with the first polarization, the transmitting light being at a low angle with respect to a normal of the optical port, and for receiving light from the optical port with the second polarization, the analyser detecting any light output from the optical port having the second polarization while filtering out light having the first polarization, in order to measure a spectral signature associated with the ring resonator.

8. The optical system according to claim 7, wherein the analyser comprises a polarizing beam splitter for separating light received from the optical port having the first polarization from light received from the optical port having the second polarization.

9. The optical system according to claim 7, wherein the analyser comprises a sensor arranged for measuring light received from the optical port having the second polarization.

10. The optical system according to claim 7, wherein the optical port comprises a two-dimensional diffraction grating structure and wherein the optical fibre is arranged for transmitting light to the optical port at an angle of less than 15 degrees with respect to a normal of the two-dimensional diffraction grating structure.

11. A method for interrogating a ring resonator in a photonic integrated circuit, the method comprising:

coupling source light having a first polarization into an optical port of the circuit;

receiving the source light from the optical port into a first waveguide of the circuit;

coupling a resonant wavelength of the source light from the first waveguide to a second waveguide via a ring resonator to form measurement light, wherein an integer number of resonant wavelengths of the light form a circumference of the ring;

returning the measurement light with the resonant wavelengths via the second waveguide to the optical port; and coupling out the light with the resonant wavelength from the optical port, wherein the optical port comprises a polarization splitting coupler that:

couples source light having the first polarization from the first waveguide; and couples measurement light having a second polarization orthogonal to the first polarization, from the second waveguide, wherein the first waveguide, the ring resonator, and the second waveguide form a looped path beginning and ending at the optical port, the first waveguide and the second waveguide intersecting at the optical port, a direction of the first waveguide being orthogonal to a direction of the second waveguide at the intersection, the source light of the first polarization coupled in the direction of the first waveguide, and returning at the intersection as the measurement light in the orthogonal direction after traversing the looped path, thereby rotating the polarization of the measurement light that exits the optical port after traversal of the looped path, as compared with polarization of the source light entering the optical port.

12. The method according to claim 11, further comprising splitting the light received from the optical port according to its polarization and measuring the split light having the second polarization.

13. The method according to claim 11, further comprising providing an optical fibre for transmitting and receiving light to and from the optical port.

* * * * *